US006835373B2

(12) United States Patent
Kolodzik et al.

(10) Patent No.: US 6,835,373 B2
(45) Date of Patent: Dec. 28, 2004

(54) NON-IRRITATING ANTIPERSPIRANT COMPOSITIONS CONTAINING ACIDIC ANTIPERSPIRANT ACTIVE

(75) Inventors: Martha Jane Kolodzik, Rising Sun, IN (US); Anthony Charles Lanzalaco, Fairfield, OH (US); David Frederick Swaile, Cincinnati, OH (US)

(73) Assignee: The Procter & Gamble Company, CT (US)

( * ) Notice: Subject to any disclaimer, the term of this patent is extended or adjusted under 35 U.S.C. 154(b) by 0 days.

(21) Appl. No.: 10/194,736

(22) Filed: Jul. 12, 2002

(65) Prior Publication Data

US 2004/0009133 A1 Jan. 15, 2004

(51) Int. Cl.[7] .............................. A61K 7/32; A61K 7/34; A61K 7/38; A61K 7/00
(52) U.S. Cl. .............................. 424/65; 424/66; 424/68; 424/400; 424/401
(58) Field of Search .............................. 424/65, 66, 68, 424/400, 401

(56) References Cited

U.S. PATENT DOCUMENTS

| 4,777,035 | A | | 10/1988 | Shin |
| 4,871,525 | A | | 10/1989 | Giovanniello et al. |
| 5,292,530 | A | | 3/1994 | McCrea et al. |
| 5,298,236 | A | | 3/1994 | Orr et al. |
| 5,356,609 | A | | 10/1994 | Giovanniello |
| 5,358,694 | A | | 10/1994 | Giovanniello |
| 5,444,096 | A | | 8/1995 | McCrea et al. |
| 5,456,906 | A | | 10/1995 | Powell et al. |
| 5,603,925 | A | | 2/1997 | Ross et al. |
| 5,855,877 | A | * | 1/1999 | Shevade et al. ............... 424/65 |
| 5,955,065 | A | * | 9/1999 | Thong et al. .................. 424/68 |
| 6,007,799 | A | | 12/1999 | Lee et al. |

FOREIGN PATENT DOCUMENTS

| EP | 0400546 A1 | 12/1990 |
| EP | 0485012 A1 | 5/1992 |
| WO | WO 9632924 | 10/1996 |
| WO | WO 9706777 | 2/1997 |

\* cited by examiner

Primary Examiner—Shelley A. Dodson
(74) Attorney, Agent, or Firm—Jack L. Oney; Vlad Vitenberg

(57) ABSTRACT

Antiperspirant compositions and corresponding methods of use comprising a particulate antiperspirant active having a metal to chloride molar ratio of less than or equal to about 1.3, a volatile solvent, a low surface tension non-volatile solvent, and a suspending agent provide reduced skin irritation and superior antiperspirant efficacy.

28 Claims, No Drawings

NON-IRRITATING ANTIPERSPIRANT COMPOSITIONS CONTAINING ACIDIC ANTIPERSPIRANT ACTIVE

FIELD OF THE INVENTION

The present invention relates to antiperspirant compositions suitable for topical application to human skin, particularly the axilla. The compositions of the present invention provide an efficacious treatment for perspiration, in combination with desired skin benefits.

BACKGROUND OF THE INVENTION

Antiperspirant actives currently used in the industry are Lewis acids. Typically, such antiperspirant actives are partially neutralized chloride salts of metal ions such as aluminum and zirconium. It is believed that, upon contact with perspiration, these materials enter the sweat duct via diffusion or convection, react with the basic (or less acidic) components of perspiration, and thereby form hydroxide plugs that block perspiration from reaching the skin surface. One route to improving the efficacy of antiperspirant actives is to increase the acidity of the active, as shown by reducing the metal to chloride molar ratio of the active.

Historically, the antiperspirant industry has migrated away from the use of antiperspirant actives having low metal to chloride molar ratios, due to the potential for increased skin irritation associated with their use. This irritation is believed to result from the degrading effect of the low pH ($\leq 3$) and high chloride level of these actives on the surface of the skin. Products in which very acidic metal salts (e.g., such as aluminum chloride) are dissolved in alcohol or aqueous solutions have been particularly problematic since, after application, the solvents would evaporate, leaving a thin "crust" of metal salt in direct contact with the skin. These residual metal salts are sensitive to moisture, and upon rewetting by moisture from the skin, produced a concentrated, highly irritating acidic solution contacting the skin surface. Nevertheless, those suffering from hyperhidrosis, or excessive perspiration, have had little choice but to use such irritating products for their efficacy.

One method of decreasing the irritation potential for acidic actives is to increase the glycine to zirconium molar ratio of the active itself, as described in U.S. Pat. No. 6,375,937, Chopra et al., issued Apr. 23, 2002. This approach increases the pH of the active, thus reducing active efficacy. Another known method of reducing the irritation potential for these actives is to encapsulate the active in a product matrix that reduces the interaction between the active and the skin surface. This can be accomplished in a wide variety of ways, including the use of non-volatile solvents, high wax levels, and encapsulation of the active in polysaccharides or starches. Unfortunately, many of the matrix components that have been used to reduce skin irritation also significantly reduce product efficacy by preventing the dissolution of the active in sweat, thereby preventing the active from entering the duct and creating a blockage.

It has now been discovered that the use of non-volatile solvents with low surface tensions reduces the irritation associated with particulate acidic antiperspirant actives having low metal to chloride molar ratios, without reducing product efficacy. It is believed that solvents with low surface tensions spread out rapidly and form a protective layer on the skin and around the active. This protective layer helps to substantially keep the acidic metal salt active particles from coming into direct contact with the skin surface. Furthermore, the protective layer provides a sufficient barrier against penetration by smaller amounts of water (e.g., transepidermal water), while still allowing for penetration by the relatively greater amounts of water produced by sweat glands (e.g., during perspiration). Perspiration easily displaces the low surface tension solvents, thereby allowing effective release of the acidic metal salt active particles from the product matrix during sweating.

SUMMARY OF THE INVENTION

The present invention is directed to antiperspirant compositions comprising a particulate antiperspirant active having a metal to chloride molar ratio of less than or equal to about 1.3; a volatile solvent; a low surface tension non-volatile solvent; and a suspending agent. The present invention is further directed to methods for controlling perspiration and hyperhidrosis through the topical application of the disclosed antiperspirant compositions. The compositions and methods of the present invention provide enhanced antiperspirant efficacy, in combination with reduced skin irritation. These and other features, aspects, and advantages of the present invention will become evident to those skilled in the art from a reading of the present disclosure.

DETAILED DESCRIPTION OF THE INVENTION

While the specification concludes with claims that particularly point out and distinctly claim the invention, it is believed the present invention will be better understood from the following description.

The present invention relates to antiperspirant compositions comprising a particulate antiperspirant active having a metal to chloride molar ratio of less than or equal to about 1.3, a volatile solvent, a low surface tension non-volatile solvent, and a suspending agent. Each of these elements will be described in detail hereinafter.

The term "ambient conditions," as used herein, refers to surrounding conditions at about one atmosphere of pressure (1 atm), at about 50% relative humidity, and at about 25° C., unless otherwise specified. All values, amounts and measurements described herein are obtained under ambient conditions, unless otherwise specified.

The term "anhydrous," as used herein, refers to compositions or materials that contain less than about 5%, more preferably less than about 3%, even more preferably less than about 1%, and still more preferably zero percent, by weight of free or added water, other than the water of hydration typically associated with any particulate solids prior to formulation.

The term "particulate," as used herein, refers to compositions or materials that are comprised of solid particles and are not dissolved in water or other solvents.

The term "surface tension," as used herein, refers to the attractive force in any liquid exerted by the molecules below the surface upon those at the surface/air interface, which force tends to restrain a liquid from flowing. The term "low surface tension," as used herein, refers to liquids having a surface tension of less than or equal to about 30 dynes.

The term "volatile," as used herein, unless otherwise specified, refers to those materials that are liquid under ambient conditions and which have a measurable vapor pressure at 25° C. These materials typically have a vapor pressure greater than about 0.01 mmHg, more typically from about 0.02 mmHg to about 20 mmHg, and an average boiling point typically less than about 250° C., more typically less than about 235° C.

All cited references are incorporated herein by reference in their entireties. Citation of any reference is not an admission regarding any determination as to its availability as prior art to the claimed invention.

All percentages, parts, and ratios as used herein are by weight of the total composition, unless otherwise specified. All such weights as they pertain to listed ingredients are based on the active level and, therefore, do not include solvents or by-products that may be included in commercially available materials, unless otherwise specified.

The antiperspirant compositions and methods of the present invention can comprise, consist of, or consist essentially of the essential elements and limitations of the invention described herein, as well as any of the additional or optional ingredients, components, or limitations described herein.

Antiperspirant Active

The antiperspirant compositions of the present invention include any particulate antiperspirant active suitable for application to human skin. The concentration of antiperspirant active in the composition should be sufficient to provide the finished antiperspirant product with the desired perspiration wetness and odor control.

The antiperspirant active used herein has a metal to chloride molar ratio of less than or equal to about 1.3. Preferably, the metal to chloride molar ratio is from about 1.3 to about 0.9, and more preferably, the ratio is about 1.25. In another embodiment of the invention, the metal to chloride molar ratio is about 0.33.

The compositions of the present invention contain particulate antiperspirant materials at concentrations ranging from about 0.1% to about 28% antiperspirant active by weight of the compositions, preferably from about 2% to about 22%, and more preferably from about 15% to about 20%. These weight percentages are calculated on an anhydrous unbuffered basis (exclusive of glycine, the salts of glycine, or other complexing agents). The particulate antiperspirant materials preferably have particle sizes of less than about 125 microns.

Particulate antiperspirant materials suitable for use herein are those that include any compound, composition or mixture thereof having antiperspirant activity. Astringent metallic salts are preferred antiperspirant materials for use herein, particularly the inorganic and organic salts of aluminum, zirconium and zinc, as well as mixtures thereof. Particularly preferred are the aluminum and zirconium salts, such as aluminum halides, aluminum hydroxy halides, zirconyl oxide halides, zirconyl hydroxy halides, and mixtures thereof.

Preferred aluminum salts are those represented by the formula:

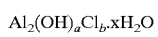
$Al_2(OH)_aCl_b \cdot xH_2O$ wherein a is from about 0 to about 4.5; the sum of a and b is about 6; x is from about 1 to about 8; and wherein a, b, and x may have non-integer values. Particularly preferred are the aluminum chlorhydroxides referred to as "¾ basic chlorhydroxide," wherein a is about 4.5, "⅔ basic chlorhydroxide," wherein a is about 4, and aluminum chloride wherein a is about 0. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980. A general description of these aluminum salts can also be found in *Antiperspirants and Deodorants*, Cosmetic Science and Technology Series Vol. 20, 2nd edition, edited by Karl Laden. Mixtures of aluminum salts are described in British Patent Specification 1,347,950, Shin et al., published Feb. 24, 1974.

Zirconium salts are also preferred for use in the antiperspirant compositions. These salts are represented by the formula:

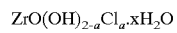
$ZrO(OH)_{2-a}Cl_a \cdot xH_2O$ wherein a is from about 0.5 to about 2; x is from about 1 to about 7; and wherein a and x may have non-integer values. These zirconium salts are described in Belgian Patent 825, 146, Schmitz, issued Aug. 4, 1975. Particularly preferred zirconium salts are those complexes that additionally contain aluminum and glycine, commonly known as ZAG complexes. Such ZAG complexes contain aluminum chlorhydroxide and zirconyl hydroxy chloride of the formulae described above. Preferred ZAG salts are described in U.S. Pat. No. 4,331,609, Orr, issued May 25, 1982. Other such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978.

Polymer size distribution of the antiperspirant actives of the compositions of the present invention can be defined by the size exclusion chromatography method as described hereinafter using Gel Permeation Chromatography (GPC).

Solid antiperspirant active salts are dissolved in 0.01M nitric acid and chromatographed using 5 $\mu$l injections in a series of three consecutive Waters $\mu$ Porasil Columns, 3.9× 300 mm, 10 $\mu$m packing. A 0.01M nitric acid mobile phase is employed. Chromatograms are visualized using a Waters 410 Differential Refractometer. Samples are prepared immediately prior to analysis to prevent degradation. Relative peak areas and area ratios are calculated using a Waters Millennium Data System (Version 2.10 or equivalent). The peaks observed in the chromatogram are designated in order of appearance on the chromatogram as Peaks I–II (appear as a single peak) and Peaks III, IV and V. The area of Peaks III, IV and V corresponds to the relative concentration of aluminum polymer species exiting the column during the specified time period from the injected sample. For aluminum-zirconium salts, the area of Peaks I–II corresponds to the relative concentration of co-eluting aluminum and zirconium polymer species appearing initially on the chromatogram.

Prior to any analysis, the columns should be conditioned individually by repeated 100 $\mu$l injections of a 10% zirconium-aluminum tetrachlorohydrate glycine solution (containing at least 10% zirconium on a solid basis). Conditioning is complete when the area percent of Peaks I–II become relatively constant. During the conditioning process, the area percent of Peaks I–II will increase, and there will be reduction in retention for all peaks. Columns should be discarded when Peaks I and II are no longer resolved from Peak III.

Preferred antiperspirant actives of the compositions of the present invention will typically have an average Peak IV area as defined by the methodology herein of at least about 7%, preferably at least about 20%, and more preferably at least about 25%.

Preferred antiperspirant actives for use in the compositions of the present invention include aluminum chloride, aluminum dichlorohydrate, aluminum sesquichlorohydrate, aluminum zirconium tetrachlorohydrate, aluminum zirconium octachlorohydrate, aluminum zirconium tetrachlorohydrate glycine, aluminum zirconium octachlorohydrate glycine, and mixtures thereof.

Volatile Solvent

The antiperspirant products of the present invention include a volatile solvent to help deliver the antiperspirant active to the skin surface in a cosmetically acceptable manner. Suitable volatile solvents for use in the antiperspirant compositions of the present invention include any hydrocarbon, silicone, or silicone-containing material that is known or otherwise suitable for topical application to the skin, provided that the volatile solvent is a liquid under ambient conditions.

The concentration of the volatile solvent in the compositions of the present invention preferably ranges from about 1% to about 75%, more preferably from about 1% to about 60%, and even more preferably from about 10% to about 50%, by weight of the composition.

Non-limiting examples of suitable volatile silicones are described in Todd et al., "Volatile Silicone Fluids for Cosmetics," Cosmetics and Toiletries, 91:27–32 (1976). Preferred among these volatile silicones are the cyclic silicones having from about 3 to about 7, more preferably from about 5 to about 6, silicon atoms. Most preferably are those that conform to the formula:

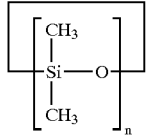

wherein n is from about 3 to about 7, preferably from about 5 to about 6, most preferably 5. These volatile cyclic silicones generally have a viscosity value of less than about 10 centistokes as measured at 25° C. Suitable volatile silicones for use herein include, but are not limited to, Cyclomethicone D-5 (commercially available from G. E. Silicones); DC 1184, DC 1735, Dow Corning 344, and Dow Corning 345 (commercially available from Dow Corning Corp.); GE 7207, GE 7158 and Silicone Fluids SF-1202 and SF-I 173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

Preferred volatile hydrocarbon liquids are branched chain hydrocarbons having the requisite volatility and which have from about 6 to about 40 carbon atoms, preferably from about 6 to about 20 carbon atoms. Specific nonlimiting examples of such combinations include the isoparaffins available from Exxon Chemical Company, Baytown, Tex. U.S.A, sold as Isopar M (C13–C14 Isoparaffin), Isopar C (C7–C8 Isoparaffin), Isopar E (C8–C9 Isoparaffin), Isopar G (C10–11 Isoparaffin), Isopar L (C11–C13 Isoparaffin), Isopar H (C11–C12 Isoparaffin), and combinations thereof. Other nonlimiting examples of suitable branched chain hydrocarbons include Permethyl 99A (C12, isododecane), Permethyl 101A (C16, isohexadecane), Permethyl 102A (C20, isoeicosane), and combinations thereof. The Permethyl series are available from Presperse, Inc., South Plainfield, N.J., U.S.A. Other nonlimiting examples of suitable branched chain hydrocarbons include petroleum distillates such as those available from Phillips Chemical as Soltrol 130, Soltrol 150, Soltrol 170, and those available from Shell as Shell Sol-70, -71, and -2033. Still other suitable isoparaffins include C9–C11 Isoparaffin, C9–C13 Isoparaffin, C9–C14 Isoparaffin, C10–C13 Isoparaffin, C12–C14 Isoparaffin, C13–C16 Isoparaffin, C14–C18 Isoparaffin, and hydrogenated polyisobutene available from Amoco as the Panalane Series and from Fanning Corporation as the Fancor P series. Nonlimiting examples of other volatile, nonpolar hydrocarbon liquids suitable for use in the antiperspirant and deodorant compositions include paraffins such as dodecane, octane, decane and combinations thereof, and the Norpar series of paraffins available from Exxon Chemical Company such as Norpar-12, -13, and -15 and the Neosolve series of paraffins available from Shell. Yet another example includes C1 I-C15 alkanes/cycloalkanes, such as those available from Exxon as Exxsol D80.

Preferably, the volatile solvent is selected from the group consisting of cyclomethicones, dimethicones, alkyl methicones, and mixtures thereof.

Low Surface Tension Non-Volatile Solvent

The compositions of the present invention include a low surface tension non-volatile solvent. Preferably, the low surface tension non-volatile solvent has a surface tension of less than or equal to about 30 dynes, more preferably from about 10 to about 30 dynes, even more preferably from about 15 to about 28 dynes, and still more preferably from about 18 to about 26 dynes. The low surface tension non-volatile solvent is present in the embodiments of the instant invention at concentrations ranging from about 1% to about 35%, preferably from about 2% to about 25%, and more preferably from about 3% to about 15% by weight of the composition.

Non-limiting examples of low surface tension non-volatile silicone liquids for use in the antiperspirant compositions of the present invention include those that conform to either of the formulas:

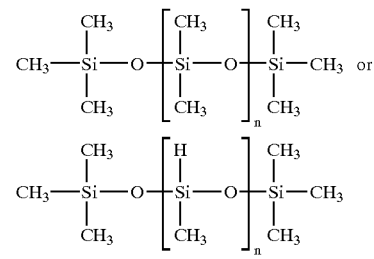

wherein n is greater than or equal to 1. These linear silicone materials will generally have viscosity values of from about 10 centistokes to about 100,000 centistokes, preferably less than about 500 centistokes, more preferably from about 10 centistokes to about 200 centistokes, even more preferably from about 10 centistokes to about 50 centistokes, as measured under ambient conditions. Non limiting examples of non-volatile, linear silicones suitable for use in the antiperspirant compositions include but are not limited to, Dow Corning 200, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

Other low surface tension non-volatile silicone solvents for use in the antiperspirant compositions of the present invention include modified or organofunctional silicone carriers such as polyalkylsiloxanes, polyalkyarylsiloxanes, cross-linked silicone elastomers, polyestersiloxanes, polyethersiloxane copolymers, polyfluorosiloxanes, polyaminosiloxanes, and combinations thereof. These modified silicone solvents are typically liquid under ambient conditions, and have a preferred viscosity of less than about 100,000 centistokes, more preferably less than about 500 centistokes, even more preferably from about 1 centistoke to about 100 centistokes, and still more preferably from about 1 centistoke to about 50 centistokes. These modified silicone solvents are generally known in the chemical arts, some examples of which are described in 1 *Cosmetics, Science and Technology* 27–104 (M. Balsam and E. Sagarin ed. 1972); U.S. Pat. No. 4,202,879, Shelton, issued May 13, 1980; and U.S. Pat. No. 5,069,897, Orr, issued Dec. 3, 1991.

Optional low surface tension non-volatile solvents for use in the instant invention may also include non-polar solvents including various hydrocarbon oils such as isoeicosane, isononyl/isononoate, octyldodecyl neopentanate, hydrogenated polyisobutane, and mixtures thereof.

Preferably, the low surface tension non-volatile solvent is selected from the group consisting of dimethicones, dimethicone copolyols, phenyl trimethicones, alkyl dimethicones, alkyl methicones, and mixtures thereof.

Suspending Agent

Another essential component of the present invention is a suspending agent. A suspending agent provides a uniform distribution of the particulate active throughout the product and may also control product rheology. A suspending agent is present in the compositions of the present invention at a concentration of from about 0.1% to about 25%, preferably from about 0.5% to about 20%, and even more preferably from about 1% to about 15% by weight of the composition.

The antiperspirant compositions of the present invention may include one or more solid crystalline or other nonpolymeric suspending agents suitable for topical application to human skin. Suitable suspending agents are those that can form in the composition a crystalline or other matrix within which volatile solvents, non-volatile solvents, or other liquid components of the composition are contained.

Suitable suspending agents for use in the composition include suspending agents that are solids under ambient conditions. These solid suspending agents preferably have a melting point of from 60° C. to about 140° C., preferably from about 60° C. to about 120° C., more preferably from about 70° C. to about 110° C. Solid suspending agents will typically and preferably be a crystalline material.

Other suspending agents suitable for use in the present antiperspirant compositions are those which can melt and form a homogenous liquid or homogenous liquid dispersion with the selected volatile and non-volatile solvent, and at the selected suspending agent and volatile and non-volatile solvent concentrations, at a processing temperature of from about 28° C. to about 125° C. The melted suspending agent is typically dispersed throughout the selected solvent system to thus form a homogenous liquid. The homogenous liquid, and other essential and optional ingredients, are preferably combined, placed in a suitable package, and then allowed to solidify and form the desired suspending agent matrix within the composition as the temperature returns to ambient temperatures and drops to below the solidification point of the selected suspending agent.

Suspending agents for use in the antiperspirant composition include fatty alcohols, esters of fatty alcohols, fatty acids, amides of fatty acids, esters or ethers of fatty acids including triglycerides, ethoxylated fatty alcohols, ethoxylated fatty acids, corresponding salts thereof, combinations thereof, and other crystalline suspending agents known or otherwise effective in providing the desired crystalline matrix within the antiperspirant composition. All such suspending agents preferably have a fatty alkyl moiety having from about 14 to about 60 carbon atoms, more preferably from about 18 to about 40 carbon atoms, and which may be saturated or unsaturated, substituted or unsubstituted, branched or linear or cyclic. Preferred fatty alkyl moieties are saturated, more preferably saturated and unsubstituted.

The term "substituted," as used herein, refers to chemical moieties known or otherwise effective for attachment to suspending agents or other compounds. Such substitutes include those listed and described in C. Hansch and A. Leo, Substituent Constants for Correlation Analysis in Chemistry and Biology (1979). Examples of such substitutes include, but are not limited to, alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Nonlimiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty alcohols may be used in the composition at concentrations preferably ranging from about 0.1% to about 8%, more preferably from about 3% to about 8%, even more preferably from about 3% to about 6%, by weight of the composition. The fatty alcohol suspending agents are also preferably saturated, unsubstituted, monohydric alcohols or combinations thereof, which have 14 to 60 carbon atoms and a melting point preferably less than about 110° C. Specific examples of fatty alcohol suspending agents for use in the antiperspirant compositions that are commercially available include, but are not limited to, Unilin 550, Unilin 700, Unilin 425, Unilin 400, Unilin 350, and Unilin 325, all supplied by Petrolite.

Suitable ethoxylated suspending agents include, but are not limited to, Unithox 325, Unithox 400, and Unithox 450, Unithox 480, Unithox 520, Unithox 550, Unithox 720, Unithox 750, all of which are available from Petrolite.

Suitable fatty acid esters for use as crystalline suspending agents include ester waxes, monoglycerides, diglycerides, triglycerides and combinations thereof. Preferred are the glyceride esters. Nonlimiting examples of suitable ester waxes including stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda and Demalcare SPS from Rhone Poulenc.

Preferred are glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant preferably has a preferred melting point of less than about 110° C. Preferred concentrations of the triglyceride suspending agents in the antiperspirant composition range from about 4% to about 20%, more preferably from about 4% to about 10%, by weight of the composition. Specific examples of preferred triglyceride suspending agents include, but are not limited to, tristearin, tribehenate, behenyl palmityl behenyl triglyceride, palmityl stearyl palmityl triglyceride, hydrogenated vegetable oil, hydrogenated rapeseed oil, castor wax, fish oils, tripalmiten, Syncrowax HRC and Syncrowax HGL-C (Syncrowax is available from Croda, Inc.). Other suitable glycerides include, but are not limited to, and glyceryl stearate and glyceryl distearate.

Suitable amide suspending agents include monoamide waxes, diamide waxes, triamide waxes, and combinations thereof, nonlimiting examples of which include cocoamide MEA (monoethanolamide), stearamide, oleamide, oleamide MEA, tallow amid monoethanolamide, and the n-acyl amino acid amide derivatives described in U.S. Pat. No. 5,429,816, Hofrichter et al., issued Jul. 4, 1995, which description is incorporated herein by reference.

Suitable fatty acid suspending agents include, but are not limited to, 12-hydroxystearic acid and derivatives thereof, behenic acid, eurcic acid, stearic acid, C20 to C40 fatty acids, and related suspending agents, some preferred examples of which are disclosed in U.S. Pat. No. 5,429,816, Hofrichter et al., issued Jul. 4, 1995; and U.S. Pat. No. 5,552,136, Motley, issued Sep. 3, 1996, both disclosures of which are incorporated by reference herein. Some commercial examples of fatty acid suspending agents include, but are not limited to, Unicid 400, available from Petrolite.

Preferred crystalline suspending agents for use in the antiperspirant compositions include coconut monoethanolamide, glyceryl tribehenate, C18–36 triglyceride, hydrogenated rapeseed oil, C20 to C40 alcohols, C20 to C40 pareth-3 and combinations thereof. Concentration of coconut monoethanolamide in the composition preferably ranges from about 5% to about 20%, more preferably from about 5% to about 15%, by weight of the composition.

Glyceryl tribehenate and hydrogenated rapeseed oil are also preferred suspending agents when used in suspending agents systems containing C20 to C40 fatty alcohols and/or C20 to C40 pareth-3, wherein the weight ratio of glyceryl tribehenate or hydrogenated rapeseed oil to C20 to C40 fatty alcohols and/or C20 to C40 pareth-3 is from about 20:1 to about 1:1, preferably from about 10:1 to about 3:1. These suspending agents are especially preferred when used in compositions containing volatile silicone solvent, especially volatile cyclomethicone, and in compositions containing a combination of a volatile silicone solvent and a low-viscosity non-volatile silicone (e.g., non-volatile dimethicones) or a non-volatile hydrocarbon solvent.

Some of the crystalline suspending agents suitable for use in the antiperspirant composition herein are also described in U.S. Pat. No. 5,552,136, Motley, issued Sep. 3, 1996; and U.S. Pat. No. 5,429,816, Hofrichter et al., issued Jul. 4, 1995; which descriptions are incorporated herein by reference.

Clays and colloidal pyrogenic silica pigments are suitable materials for use as suspending agents in the present invention. Colloidal silica is available commercially as Cab-O-Sil®, a submicroscopic particulated pyrogenic silica.

Clay suspending agents suitable for use in the compositions of the present invention are selected from the group consisting of montmorillonite clays and hydrophobically treated montmorillonite clays. Montmorillonite clays are those that contain mineral montmorillonite and are characterized by having a suspended lattice. Examples of these clays include the bentonites, hectorites, and colloidal magnesium aluminum silicates.

Bentonite is a colloidal, hydrated aluminum silicate obtained from montmorillonite and has the formula $Al_2O_3 4SiO_2.H_2O$. A more detailed discussion can be found in the KIRK-OTHMER ENCYCLOPEDIA OF CHEMICAL TECHNOLOGY, 2d ed., Vol. 3 (1964), pp. 339–360, published by Interscience Publishers. Hectorite, also a montmorillonite clay, differs from bentonite in that there is almost a complete substitution of aluminum in the lattice structure of bentonite by magnesium. In addition, hectorites contain lithium and fluorine. Laponite is an example of a commercially available synthetic hectorite marketed by Laporte Industries, Ltd.

The magnesium aluminum silicates are complexes of colloidal magnesium aluminum silicate, richer in magnesium than aluminum. Magnesium aluminum silicates are commercially available as Veegum (R.T. Vanderbilt Co.).

Preferred clay suspending agents for use in the present invention are certain hydrophobically treated montmorillonite clays, e.g., hydrophobic bentonites available under the trade name "Bentone." Bentone is prepared by reacting bentonite in a cation exchange system with an amine. Different amines are reacted to obtain a variety of Bentones, which may also differ in proportions of $SiO_2$, MgO, and $Al_2O_4$. Specific examples of Bentones within the scope of the present invention are Bentone 38, Bentone 34, Bentone 27, Bentone 14, and Bentone LT, all of which have a particle size of below about 5 microns and are commercially available from NL Industries, Inc.

Preferably, the suspending agent is selected from the group consisting of silica, Bentonite clays, tribehenin, C18–C36 acid triglyceride, hydrogenated castor oil, hydrogenated rapeseed oil, stearyl alcohol, behenyl alcohol, 12-hydroxystearic acid, Dibutyl Lauroyl glutamide, and mixtures thereof.

Product Form

The antiperspirant compositions of the present invention can be formulated in any liquid, solid, or semi-solid form, provided that the selected form contains all the essential elements as defined herein. These compositions can be formulated as opaque, translucent, or clear formulations. The antiperspirant compositions of the present invention are preferably packaged into any container or applicator suitable for use in applying the composition to the axilla.

Methods of Use

The antiperspirant compositions of the present invention are formulated in final form to be topically applied to the axilla or other area of the skin to reduce perspiration and malodor. The compositions of the present invention are further formulated to be topically applied to the axilla or other area of the skin to treat hyperhidrosis. These methods comprise applying to the axilla or other area of the skin a safe and effective amount the antiperspirant composition of the present invention. In this context, the term "safe and effective amount" means an amount of the antiperspirant composition topically applied to the skin that is effective in inhibiting or minimizing odor and perspiration at the site of application while also being safe for topical use at a reasonable risk/benefit ratio. In this context, a safe and effective amount typically ranges from about 0.1 gram per axilla to about 2.0 grams per axilla. The compositions are preferably applied to the skin one or more times daily, preferably once daily.

EXAMPLES

The following Examples I–V illustrate specific embodiments of the antiperspirant compositions and methods of manufacture of the present invention, but are not intended to be limiting thereof. Other modifications can be undertaken by the skilled artisan without departing from the spirit and scope of this invention.

Each exemplified composition is applied topically to the axilla in an amount effective to inhibit or prevent perspiration, typically an amount ranging from about 0.1 gram to about 2.0 grams per axilla. The applied compositions are effective in inhibiting perspiration and malodor from the applied areas, and cause little or no skin irritation. All exemplified amounts are weight-weight percentages of raw materials based upon total weight of the composition, unless otherwise specified.

TABLE 1

Antiperspirant Compositions

|  | I | II | III | IV | V |
|---|---|---|---|---|---|
| Alumium Chloride hexahydrate[a] | 14.9 | | | | |
| Aluminum Dichlorohydrate[b] | | | 25 | | |
| Aluminum Zirconium Tetrachlorohydrate glycine[c] | | 25 | | 25 | 25 |
| Cyclopentasiloxane | 72.3 | 57 | 47 | 48 | 43 |
| Dimethicone (10 Cst) | 5.7 | 10 | | | |
| Dimthicone (350 Cst) | | | 20 | | |
| Tribehenin | 5.7 | 6 | | | |
| C18–C36 Acid Triglyceride | 1.4 | 2 | | | |
| Silica[d] | | | 3 | | |
| Microthene[e] | | | 5 | | 6 |
| Octyl dodecanol | | | | 14 | |
| 12-hydroxystearic acid | | | | 7 | |
| Dibutyl Lauroyl glutamide | | | | 2 | |
| C20–40 Pareth 10 | | | | 1.65 | |
| C20–40 Pareth 40 | | | | 1.65 | |
| Alcohol C20–40 | | | | 0.5 | |
| Disodium EDTA | | | | 0.2 | |
| Mineral oil | | | | | 20 |
| Quaternium 18-hectorite | | | | | 4 |
| Proylene Carbonate | | | | | 1 |
| Dipropylene glycol | | | | | 1 |

[a]Metal to chloride molar ratio = 0.33; 55% anhydrous active level (Sigma Chemical Company)
[b]Metal to chloride molar ratio = 1.2; 85% anhydrous active level
[c]Metal to chloride molar ratio = 1.25; 75% anhydrous unbuffered active level (Westwood Chemical Co.)
[d]Cab-O-Sil ®, Purchased from Cabot Corp.
[e]Purchased from Quantum Chemical Corp.

Methods of Manufacture for Examples I–II

The compositions described in Examples I–II are formulated by first adding the cyclopentasiloxane and dimethicone to a beaker and heating to 80° C. The tribehenin and C18–C36 acid triglyceride are then added with stirring and held until melted. Next, the particulate active is added and the product is cooled to 55° C. The composition is then poured into an appropriate container.

Method of Manufacture for Example III

The composition described in Example III is formulated by first adding the cyclopentasiloxane and dimethicone to a stainless steel mixing vessel. The Cab-O-Sil® is then added, followed by the Microthene and, finally, the antiperspirant active. The composition is thoroughly stirred after addition of each particulate material. The composition is then milled, using a Black and Decker Die Grinder (Model 4420, type 4) with a 6.35 cm diameter Cowles dispersing blade at approximately 6000 rpm, for approximately 5 minutes.

Method of Manufacture for Example IV

The composition described in Example IV is formulated by first adding the cyclopentasiloxane and octyl dodecanol to a beaker and heating to 85° C. Next, the 12-hydroxystearic acid, Dibutyl Lauroyl glutamide, C20–40 Pareth 10, C20–40 Pareth 40, and Alcohol C20–40 are added with stirring and held until melted. Next, the particulate active and disodium EDTA are added and the product is cooled to about 60° C. and then poured into an appropriate container.

Method of Manufacture for Example V

The composition described in Example V is formulated by first adding the cyclopentasiloxane, mineral oil, dipropylene glycol, and propylene carbonate to a stainless steel mixing vessel. The Quaternium-18 hectrorite is then added, followed by the Microthene and, finally, the antiperspirant active. The composition is thoroughly stirred after addition of each particulate material. The composition is then milled, using a Black and Decker Die Grinder (Model 4420, type 4) with a 6.35 cm diameter Cowles dispersing blade at approximately 6000 rpm, for approximately 5 minutes.

The above embodiments have been described by way of example only. Many other embodiments falling within the scope of the accompanying claims will be apparent to the skilled reader.

What is claimed is:

1. An antiperspirant composition comprising:
    a) a particulate antiperspirant active having a metal to chloride molar ratio of less than or equal to about 1.3;
    b) a volatile solvent;
    c) a low surface tension non-volatile solvent, having a surface tension of less than or equal to about 30 dynes; and
    d) a suspending agent.

2. An antiperspirant composition according to claim 1 wherein the composition comprises:
    a) from about 0.1% to about 28% by weight on an anhydrous unbuffered basis of the particulate antiperspirant active;
    b) from about 1% to about 75% by weight of the volatile solvent;
    c) from about 1% to about 35% by weight of the low surface tension non-volatile solvent; and
    d) from about 0.1% to about 25% by weight of the suspending agent.

3. An antiperspirant composition according to claim 1 wherein the particulate antiperspirant active has a metal to chloride molar ratio of from about 1.3 to about 0.9.

4. An antiperspirant composition according to claim 3 wherein the particulate antiperspirant active has a metal to chloride molar ratio of about 1.25.

5. An antiperspirant composition according to claim 1 wherein the particulate antiperspirant active has a metal to chloride molar ratio of about 0.33.

6. An antiperspirant composition according to claim 1 wherein the particulate antiperspirant active is selected from the group consisting of aluminum chloride, aluminum dichlorohydrate, aluminum sesquichlorohydrate, aluminum zirconium tetrachlorohydrate, aluminum zirconium octachlorohydrate, aluminum zirconium tetrachlorohydrate glycine, aluminum zirconium octachlorohydrate glycine, and mixtures thereof.

7. An antiperspirant composition according to claim 1 wherein the particulate antiperspirant active has a Peak IV area of at least about 25%.

8. An antiperspirant composition according to claim 2 wherein the composition comprises from about 2% to about 22% by weight on an anhydrous unbuffered basis of the particulate antiperspirant active.

9. An antiperspirant composition according to claim 8 wherein the composition comprises from about 15% to about 20% by weight on an anhydrous unbuffered basis of the particulate antiperspirant active.

10. An antiperspirant composition according to claim 1 wherein the particulate antiperspirant active has a particle size of less than about 125 microns.

11. An antiperspirant composition according to claim 1 wherein the volatile solvent is a silicone.

12. An antiperspirant composition according to claim 1 wherein the volatile solvent is selected from the group consisting of cyclomethicones, dimethicones, alkyl methicones, and mixtures thereof.

13. An antiperspirant composition according to claim 2 wherein the composition comprises from about 1% to about 60% by weight of the volatile solvent.

14. An antiperspirant composition according to claim 13 wherein the composition comprises from about 10% to about 50% by weight of the volatile solvent.

15. An antiperspirant composition according to claim 1 wherein the low surface tension non-volatile solvent is selected from the group consisting of dimethicones, dimethicone copolyols, phenyl trimethicones, alkyl dimethicones, alkyl methicones, and mixtures thereof.

16. An antiperspirant composition according to claim 2 wherein the composition comprises from about 2% to about 25% by weight of the low surface tension non-volatile solvent.

17. An antiperspirant composition according to claim 16 wherein the composition comprises from about 3% to about 15% by weight of the low surface tension non-volatile solvent.

18. An antiperspirant composition according to claim 17 wherein the low surface tension non-volatile solvent has a surface tension of from about 10 to about 30 dynes.

19. An antiperspirant composition according to claim 18 wherein the low surface tension non-volatile solvent has a surface tension of from about 15 to about 28 dynes.

20. An antiperspirant composition according to claim 19 wherein the low surface tension non-volatile solvent has a surface tension of from about 18 to about 26 dynes.

21. An antiperspirant composition according to claim 1 wherein the suspending agent is selected from the group consisting of silica, Bentonite clays, tribehenin, C18–C36 acid triglyceride, hydrogenated castor oil, hydrogenated rapeseed oil, stearyl alcohol, behenyl alcohol, 12-hydroxystearic acid, Dibutyl Lauroyl glutamide, and mixtures thereof.

22. An antiperspirant composition according to claim 2 wherein the composition comprises from about 0.5% to about 20% by weight of the suspending agent.

23. An antiperspirant composition according to claim 22 wherein the composition comprises from about 1% to about 15% by weight of the suspending agent.

24. An antiperspirant composition according to claim 1 wherein the composition is a solid.

25. An antiperspirant composition according to claim 1 wherein the composition is a semi-solid.

26. An antiperspirant composition according to claim 1 wherein the composition is a liquid.

27. A method of reducing perspiration comprising the topical application of from about 0.1 gram to about 2.0 grams per axilla of the antiperspirant composition of claim 1.

28. A method of treating hyperhidrosis comprising the topical application of from about 0.1 gram to about 2.0 grams per axilla of the antiperspirant composition of claim 1.

* * * * *